United States Patent [19]
Kennedy

[11] Patent Number: 5,935,166
[45] Date of Patent: Aug. 10, 1999

[54] IMPLANTABLE HEARING ASSISTANCE DEVICE WITH REMOTE ELECTRONICS UNIT

[75] Inventor: Joel A. Kennedy, Arden Hills, Minn.

[73] Assignee: St. Croix Medical, Inc., Minneapolis, Minn.

[21] Appl. No.: 08/755,181

[22] Filed: Nov. 25, 1996

[51] Int. Cl.⁶ ........................................................ A61F 2/18
[52] U.S. Cl. ................................ 623/10; 607/56; 607/57; 600/25
[58] Field of Search ................................ 600/25; 607/56, 607/57; 623/10

[56] References Cited

U.S. PATENT DOCUMENTS

| | | | |
|---|---|---|---|
| 4,150,262 | 4/1979 | Ono | 179/107 BC |
| 4,606,329 | 8/1986 | Hough | 128/1 R |
| 4,612,915 | 9/1986 | Hough et al. | 128/1 R |
| 4,729,366 | 3/1988 | Schaefer et al. | 128/1.6 |
| 4,850,962 | 7/1989 | Schaefer | 600/25 |
| 5,282,858 | 2/1994 | Bisch et al. | 623/10 |
| 5,558,618 | 9/1996 | Maniglia | 600/25 |
| 5,571,148 | 11/1996 | Loeb et al. | 607/57 |
| 5,603,726 | 2/1997 | Schulman et al. | 607/57 |

OTHER PUBLICATIONS

"Issues and Answers—The Nucleus 22 Channel Cochlear Implant System", Product Brochure published by Cochlear Corporation, 34 pgs (1995).

Staller, S.J., "Cochlear Implants: A Changing Technology", *The Hearing Journal*, vol. 49, No. 3, pp. 10, 58–60, 62, 64 (Mar. 1996).

*Primary Examiner*—Paul B. Prebilic
*Attorney, Agent, or Firm*—Patterson & Keough, P.A.

[57] ABSTRACT

An implantable hearing assistance system has a subcranially implantable electronics unit that is remotely situated from the ear, such as implanted in the pectoral region, rather than in the mastoid portion of the temporal bone. The increased volume available in the remote electronics unit allows it to carry a power source of increased energy capacity. This improves longevity, allows higher power consumption signal processing capability, and simplifies battery replacement. The hearing assistance system is coupled to a middle ear input transducer and a middle or inner ear output stimulator. The hearing assistance system is capable of use in a partial middle ear implantable (P-MEI), total middle ear implantable (T-MEI), or cochlear implant hearing assistance system.

18 Claims, 5 Drawing Sheets

IMPLANTABLE HEARING ASSISTANCE DEVICE WITH REMOTE ELECTRONICS UNIT

THE FIELD OF THE INVENTION

This invention relates to an at least partially implantable hearing assistance system or cochlear implant.

BACKGROUND

In some types of partial middle ear implantable (P-MEI) or total middle ear implantable (T-MEI) hearing assistance systems, sounds produce mechanical vibrations which are transduced by an electromechanical input transducer into electrical signals. These electrical signals are in turn provided to an electronics unit which amplifies the signal and provides it to an electromechanical output transducer. The electromechanical output transducer typically vibrates an ossicular bone in response to the applied amplified electrical signals, thus improving hearing.

Such systems, as well as other hearing assistance systems, typically face limitations on processing capability and longevity due to the limited energy capacity of implanted batteries. This is particularly true for conventional P-MEI hearing assistance systems having a battery disposed in the electronics unit, which is implanted in the mastoid region of the temporal bone behind the ear. There is a need in the art for a hearing assistance system that provides increased battery capacity, which would ease the limitations on processing capability and longevity. There is a further need in the art for a hearing assistance system that allows convenient battery replacement.

SUMMARY

The present invention provides a hearing assistance system having an electronics unit that is remotely situated from the ear, thereby realizing several advantages. The hearing assistance system of the present invention includes an electromechanical input transducer, which is proportioned for disposition within a middle ear region of a first ear, for converting a mechanical sound vibration into an input electrical signal. An output stimulator is proportioned for disposition within the middle ear region or an inner ear region of a second ear. An electronics unit is proportioned for subcutaneous subcranial implantation. The electronics unit provides an output electrical signal in response to the input electrical signal. An input link communicates the input electrical signal between the input transducer and the subcranially implanted electronics unit. An output link communicates the output electrical signal between the output stimulator and the subcranially implanted electronics unit.

The first and second ears may be the same ear, or different ears. In one embodiment, the output stimulator is an electromechanical transducer for converting an electrical signal into a mechanical sound vibration. In another embodiment, the output stimulator is a cochlear implant for delivering electrical stimuli to the inner ear. The electronics unit is, in one embodiment, proportioned for pectoral implantation.

The hearing assistance system operates according to a method that includes receiving a mechanical sound vibration from an electromechanical input transducer that is proportioned for disposition within a middle ear region of a first ear, and providing an input electrical signal in response thereto. The input electrical signal is communicated to a subcranially implanted electronics unit that provides an output electrical signal in response thereto. The output electrical signal is communicated to an output stimulator that is proportioned for disposition within the middle ear region or an inner ear region of a second ear. The output stimulator provides output stimuli to the middle or inner ear in response to the output electrical signal.

By providing a hearing assistance system having an electronics unit that is remotely situated from the ear, a larger volume is available than if implanted in the mastoid region of the temporal bone behind the ear. The larger electronics unit, in turn, carries therein a larger volume power source having increased energy capacity. This provides several advantages, including: increased longevity of the implantable hearing assistance system before battery replacement is required; more convenient battery replacement, such as when the electronics unit is pectorally implanted; and allowing for higher power consumption signal processing capabilities.

BRIEF DESCRIPTION OF THE DRAWINGS

In the drawings, like numerals describe substantially similar components throughout the several views.

DETAILED DESCRIPTION

Figure 1:
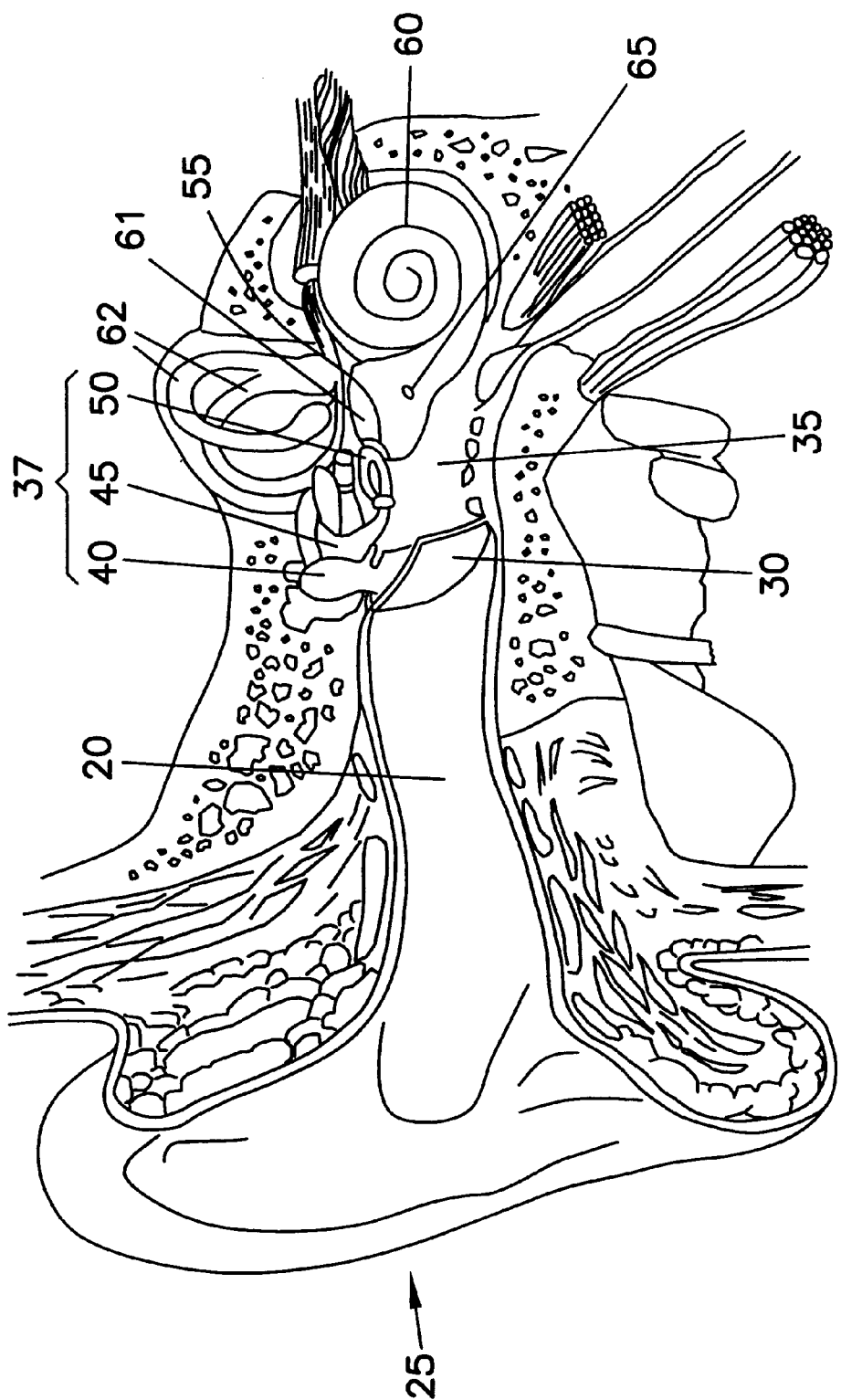
FIG. 1 illustrates a frontal section of an anatomically normal human ear in which the invention operates.

The invention provides a hearing assistance system capable of use as or with a middle ear implantable hearing system such as a partial middle ear implantable (P-MEI), total middle ear implantable (T-MEI), cochlear implant, or other hearing system. A P-MEI or T-MEI hearing system assists the human auditory system in converting acoustic energy contained within sound waves into electrochemical signals delivered to the brain and interpreted as sound. FIG. 1 illustrates generally a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three primary components: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing systems have also been developed, utilizing various approaches to compensate for hearing disorders. For example, cochlear implant techniques implement an inner ear hearing system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing systems have been developed to aid patients without an intact tympanic membrane 30, upon which "air conduction" hearing aids depend. For example, temporal bone conduction hearing systems produce mechanical vibrations that are coupled to the cochlea 60 via a temporal bone in the skull. In such temporal bone conduction hearing systems, a vibrating element can be implemented percutaneously or subcutaneously.

A particularly interesting class of hearing systems includes those which are configured for disposition principally within the middle ear 35 space. In middle ear implantable (MEI) hearing assistance systems, an electrical-to-mechanical output transducer couples mechanical vibrations to the ossicular chain 37, which is optionally interrupted to allow coupling of the mechanical vibrations to the ossicular chain 37. Both electromagnetic and piezoelectric output transducers have been used to effect the mechanical vibrations upon the ossicular chain 37.

One example of a partial middle ear implantable (P-MEI) hearing system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption requiring larger batteries, which limits their usefulness in total middle ear implantable (T-MEI) hearing systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed by an electronics unit. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

In the '366 patent, a power source and electronic circuits are disposed in a surgically developed antrum in the mastoid bone of the subject's skull. A limited volume is available for creating such a cavity. As a result, the volume and energy capacity of the power source is correspondingly limited as well. This limits both processing capability and longevity of such a device. Furthermore, it is inconvenient to replace the power source since it is implanted in the mastoid bone.

The present invention provides a hearing assistance system having an electronics unit that is remotely situated from the ear, thereby realizing several advantages as explained below. The invention is capable of use as or with a MEI hearing assistance system, such as a P-MEI or T-MEI hearing assistance system. The invention is also capable of use with a variety of piezoelectric, electromagnetic, and other transducers. The invention is also capable of use as or with a cochlear implant system, such as a single channel or multichannel cochlear implant, or other cochlear implant.

Figure 2:
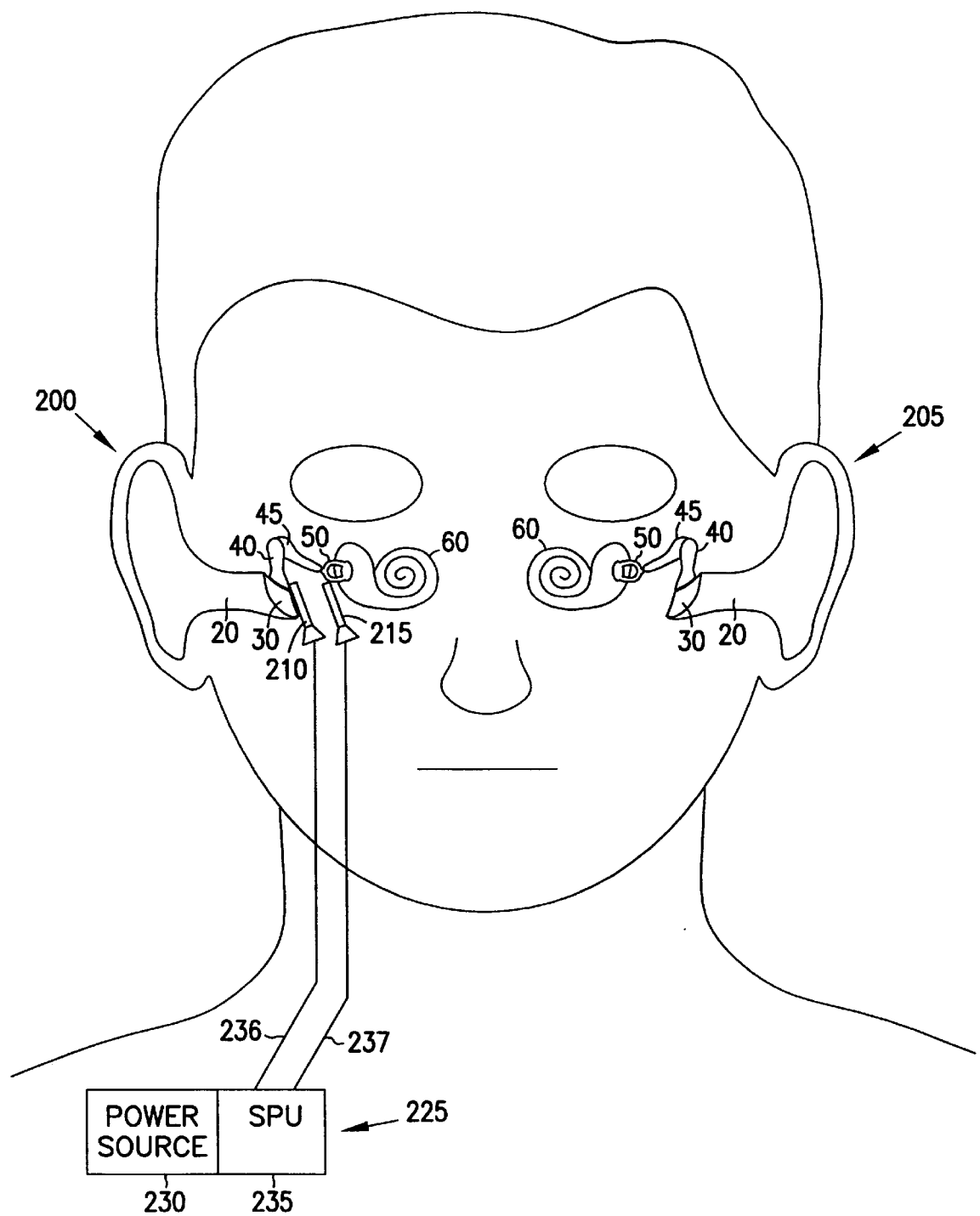
FIG. 2 is a generalized schematic illustration of a frontal view of a person with cutaway views each ear, including one embodiment of the invention partially disposed in one ear.

FIG. 2 is a generalized schematic illustration of one embodiment of the invention. FIG. 2 illustrates a frontal view of a person with cutaway views of the anatomical features of each of a right ear 200 and a left ear 205. An electromechanical input transducer 210 is disposed within the middle ear 35 region of right ear 200. In one embodiment, input transducer 210 is mechanically coupled, such as to tympanic membrane 30, malleus 40, incus 45, or other auditory element, for receiving mechanical sound vibrations that are converted into an input electrical signal. In another embodiment, input transducer 210 is a microphone for receiving sound vibrations that are converted into the input electrical signal. An output stimulator, such as electromechanical output transducer 215 is disposed within middle ear 35 region of right ear 200, and mechanically coupled to an auditory element such as stapes 50.

Input and output transducers 210 and 215, respectively, are either freestandingly coupled to their respective auditory elements, or also rigidly mounted elsewhere, such as to the temporal bone in the middle ear 35 region. Input transducer 210 typically includes at least one piezoelectric element such as a piezoelectric crystal, ceramic, or polymer. Output transducer 215 typically includes at least one similar piezoelectric element, or an electromagnetic or other suitable transducer type. Incus 45 is optionally removed to prevent mechanical feedback from output transducer 215 to input transducer 210 through incus 45.

Electronics unit 225 is remotely disposed from input transducer 210 and output transducer 215. More particularly, electronics unit 225 is located away from the middle ear and away from the mastoid region of the temporal bone. Instead, electronics unit 225 is typically subcranially implanted. For example, electronics unit 225 is typically proportioned for implantation in the person's pectoral region, or some other convenient location. Electronics unit 225 typically contains a power source 230, such as a battery, and signal processing unit 235. Since electronics unit 225 of the present invention need not be implanted in the mastoid region of the temporal bone, its volume may be increased.

For example, implantation in the mastoid region of the temporal bone typically limits the volume of electronics unit 225 to approximately 2 cubic centimeters. Since electronics unit 225 of the present invention need not be implanted in the mastoid region of the temporal bone, its volume may be increased, such as to exceed approximately 10 cubic centimeters. Power source 230, contained within electronics unit 225, may correspondingly increase in both volume and energy capacity. Current battery technology typically has a volumetric energy density limited to approximately 0.4 ampere-hours per cubic centimeter. If the power source occupies most of the volume the electronics unit in which it is contained, then battery capacity would be limited to approximately 0.8 ampere-hours when implanted in the mastoid region of the temporal bone. Battery capacity increases to approximately 4 ampere-hours when implanted in the pectoral or other region, according to the present invention. Assuming the electronics unit requires 20 microamperes for operation, the increased battery capacity translates into an increase in device longevity from approximately 4.5 years to approximately 22 years. Thus, the present invention is capable of providing a power source having an energy capacity well exceeding 1 ampere-hour, as explained above.

The increased energy capacity of power source 230 may be used to increase the implanted longevity of the hearing assistance system before replacement of power source 230 is needed. Alternatively, higher power consumption functionality may be incorporated in signal processing unit 235. For example, a digital signal processor may be included in signal processing unit 235. The increased energy capacity of power source 230 may also be used to achieve some combination of increased longevity and higher power consumption functionality. When subcranially implanted in the pectoral region, electronics unit 225 is easier to explant than when disposed in the mastoid portion of the temporal bone. This simplifies the procedure of replacing power source 230 when its useful energy capacity is exhausted.

In one embodiment, input transducer 210 is electrically coupled through an input link, such as input lead 236, for providing the input electrical signal to electronics unit 225. Similarly, electronics unit 225 is electrically coupled through an output link, such as output lead 237, for providing the output electrical signal to the output stimulator, such as output transducer 215. Input and output leads 236 and 237, respectively, are typically implemented separately, although a single integrally formed lead could be used to combine input and output leads 236 and 237, respectively.

In one embodiment, at least one of input and output leads 236 and 237 provides AC coupled communication, such as by a series capacitor, between electronics unit 225 and at least one of input transducer 210 and the output stimulator, such as output transducer 215. Such AC coupled communication is advantageous in reducing or eliminating potential dendrite growth, which is the formation of tissue occurring when a DC electric field is passed through bodily fluids. Such dendrites are typically conductive and might degrade performance of the input transducer 210 and the output stimulator, such as output transducer 215, or other circuits.

Input and output leads 236 and 237 are subcutaneously disposed. For example, in one embodiment where electronics unit 225 is pectorally implanted, input and output leads 236 and 237 extend subcutaneously from the pectoral region, along the neck region, and through an access hole created in a mastoid portion of the temporal bone anterior to outer ear 20 region of right ear 200.

In one embodiment, input and output leads 236 and 237, respectively, are individually mechanically coupled to receptacles on respective input and output transducers 210 and 215. In another embodiment, input and output leads 236 and 237, respectively, are mechanically coupled to receptacles on the one or more mounts to which respective input and output transducers 210 and 215 are affixed, and the receptacles are individually electrically coupled to one of input and output transducers 210 and 215, respectively. In another embodiment, respective input and output leads 236 and 237 are mechanically coupled to a coupler optionally located outside middle ear 35 region for more convenient access, and the coupler is itself individually electrically coupled to each one of the input and output transducers 210 and 214, respectively.

In one embodiment, respective input and output leads 236 and 237 are each longer than 2 inches. More particularly, the input and output leads 236 and 237, respectively, will extend from electronics unit 225, which is remotely implanted such as in the pectoral region, and an middle ear 35 or inner ear region on the same or opposite side of the subject's body. Input and output leads 236 and 237, respectively, will typically range from between 2 inches and 12 inches in length, but these lengths will vary according to individual physiology and exact location of the implanted electronics unit 225.

Input and output leads 236 and 237, respectively, include at least one, and typically more than one, conductor that is capable of withstanding flexion stresses such as from muscle movement. For example, the conductors may be of nickel alloy wires manufactured with a drawn-brazed-strand (DBS) technique to resist flexion related fractures, although other suitable conductor materials and manufacturing techniques may also be used. The conductors are typically insulated from each other and from the subject's body by insulation comprising silicone rubber or other suitable insulation material. Input and output leads 236 and 237, respectively, may also include connectors for engaging receptacles on input and output transducers 210 and 215, respectively, or on associated mounts or couplers, and also for engaging receptacles on electronics unit 225.

Figure 3:
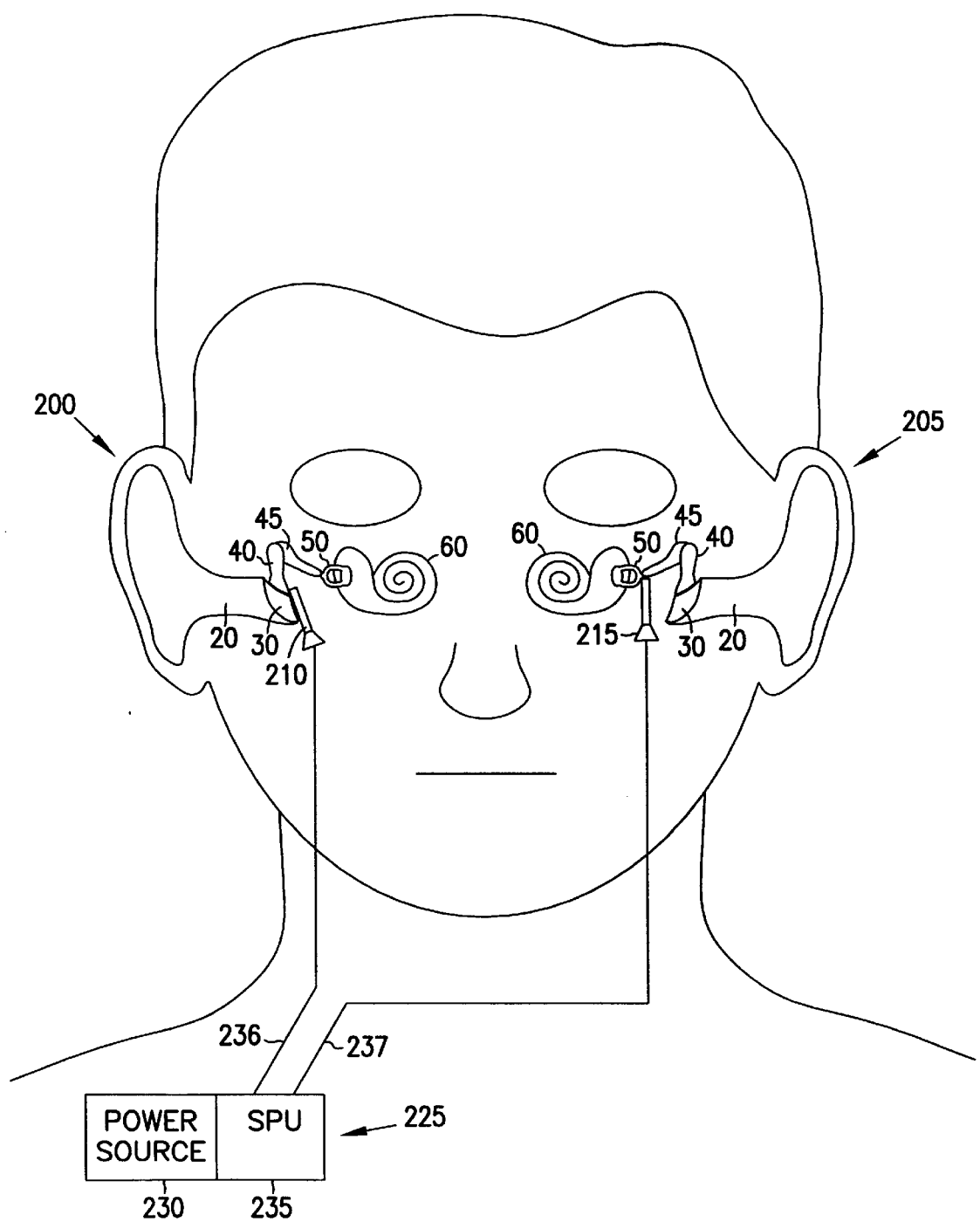
FIG. 3 is a generalized schematic illustration of a frontal view of a person with cutaway views each ear, including a second embodiment of the invention partially disposed in each ear.

FIG. 3 is a generalized schematic illustration of another embodiment of the invention including a frontal view of a person in which it is used. In FIG. 3, input transducer 210 is disposed within middle ear 35 of right ear 200 and output transducer 215 is disposed within middle ear 35 of left ear 205, or vice-versa, using similar techniques to those described above. Input and output transducers 210 and 215 are respectively coupled through input lead 236 and output lead 237 to electronics unit 225 in a similar manner as described above. The embodiment of FIG. 3 is particularly useful when right ear 200 has severe sensorineural hearing loss such that the output stimulator provides it with no benefit. In that case, mechanical sound vibrations received in the right ear 200 may be communicated to the left ear 205 for output stimulation and interpretation by the subject's auditory system.

Figure 4:
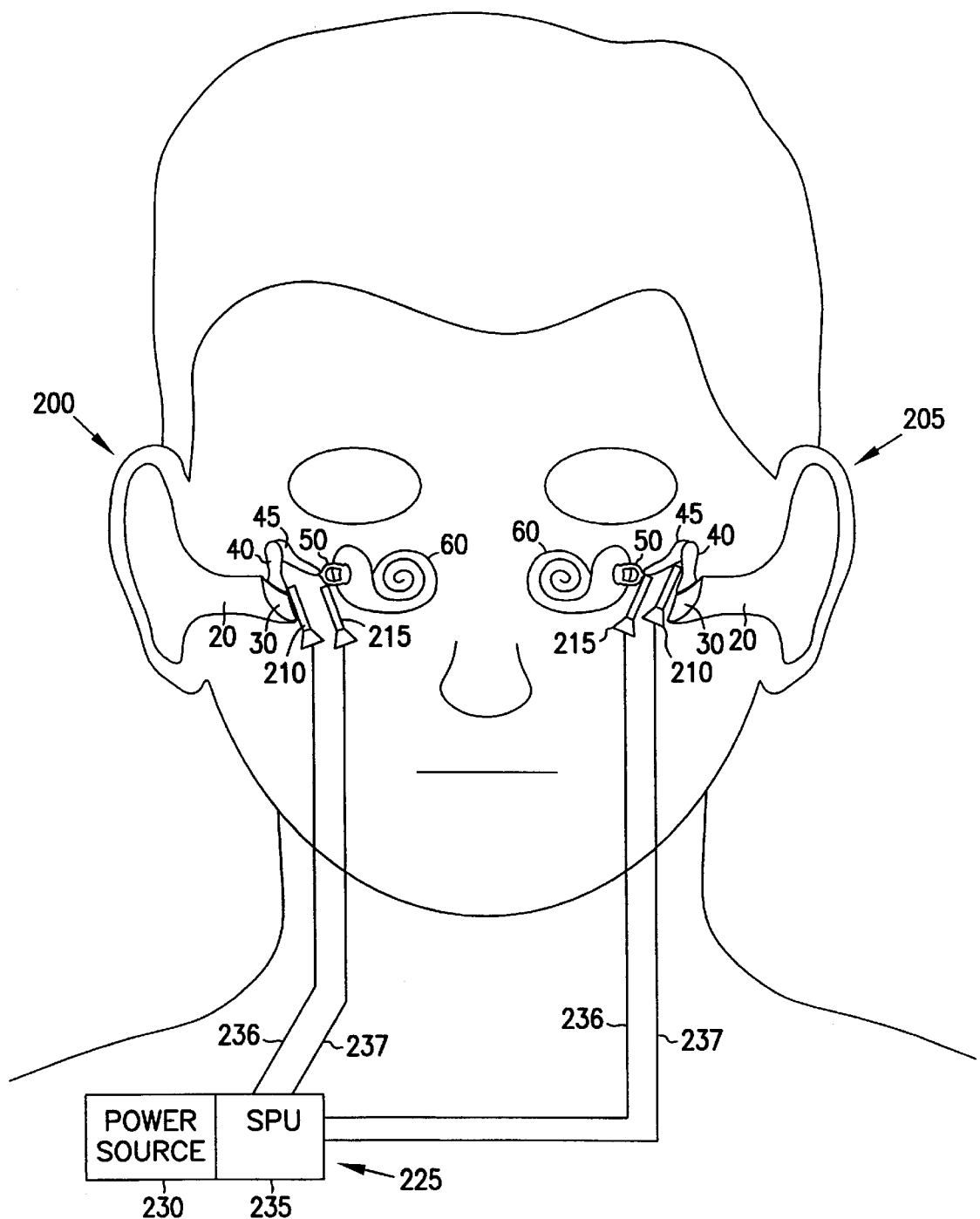
FIG. 4 is a generalized schematic illustration of a frontal view of a person with cutaway views of each ear, including a third embodiment of the invention that is partially disposed in each ear and has dual input and output paths.

FIG. 4 is a generalized schematic illustration of another embodiment of the invention including a frontal view of a person in which it is used. FIG. 4 includes the features of the present invention with respect to the right ear 200, as illustrated in FIG. 2, and adds similar features with respect to the left ear 205. More particularly, additional instances of input and output transducers 210 and 215, respectively, are disposed in left ear 205, and electrically coupled to electronics unit 225 through input and output links such as the respective instances of input and output leads 236 and 237 associated with left ear 205. In this embodiment, the invention implements a dual path hearing assistance system. One example of dual path hearing assistance system functionality is described in co-pending patent application entitled DUAL PATH IMPLANTABLE HEARING ASSISTANCE DEVICE, filed on even date with the present application, assigned to the assignee of the present application, and which is herein incorporated by reference.

Figure 5:
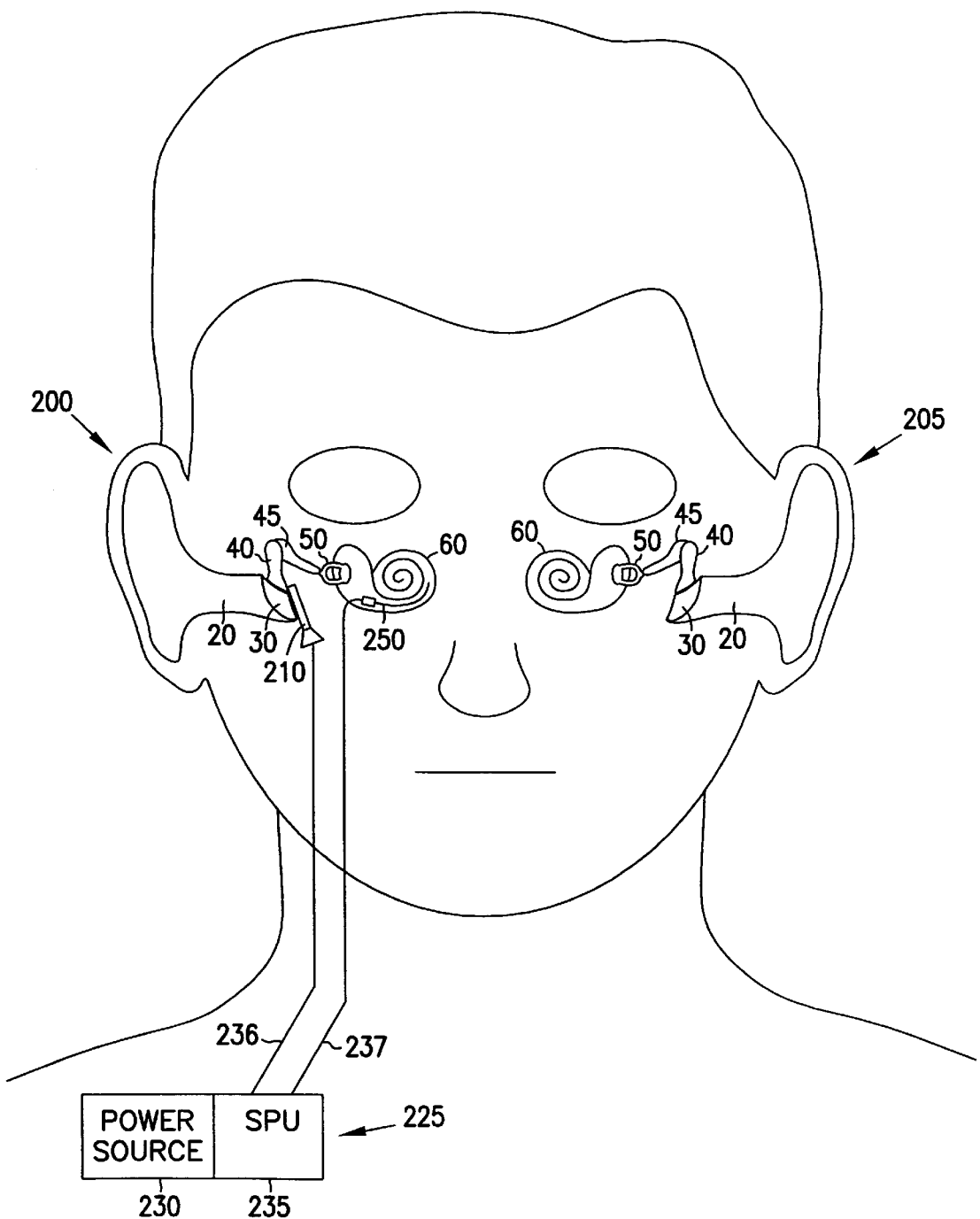
FIG. 5 is a generalized schematic illustration of a frontal view of a person with cutaway views of each ear, including a fourth embodiment of the invention comprising a cochlear implant output stimulator.

FIG. 5 is a generalized schematic illustration of another embodiment of the invention including a frontal view of a person in which it is used. FIG. 5 includes some of the features of the invention described with respect to FIG. 2, but the output stimulator comprises a single channel or multiple channel cochlear implant 250 rather than output transducer 215. Cochlear implant 250 is disposed in cochlea 60 by insertion either through the oval window 55, round window 65, or elsewhere, or disposed elsewhere in the inner ear region. In this embodiment, signal processing unit 235 includes cochlear implant processing capability, and output lead 237 includes an appropriate configuration of conductors corresponding to the particular single channel or multiple channel cochlear implant 250.

Thus, the present invention provides an implantable hearing assistance system having an implantable electronics unit that is remotely situated from the ear, rather than implanted in the mastoid portion of the temporal bone. The increased volume available in the remote electronics unit allows a power source contained therein, which has increased energy capacity. This improves longevity, enhances processing capability, and simplifies battery replacement.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A hearing assistance system comprising:
    an electromechanical input transducer, proportioned for disposition within a middle ear region of a first ear, for converting a mechanical sound vibration into an input electrical signal;
    an output stimulator, proportioned for disposition within the middle ear region of the first ear; and
    an electronics unit having volume exceeding approximately 10 cubic centimeters, electrically connected between the input transducer and the output stimulator and proportioned only for subcutaneous pectoral implantation, wherein the electronics unit receives the input electrical signal from the input transducer and provides an output electrical signal to the output stimulator in response to the input electrical signal.

2. The hearing assistance system of claim 1, wherein the output stimulator is an electromechanical transducer for converting an electrical signal into a mechanical sound vibration.

3. The hearing assistance system of claim 1, wherein the output stimulator is a cochlear implant for delivering electrical stimuli to the inner ear.

4. The hearing assistance system of claim 1, and further comprising:

an input link electrically connecting the input transducer to the electronics unit and an output link electrically connecting the electronics unit to the output stimulator, wherein each of the input and output links includes an implantable lead.

5. The hearing assistance system of claim 4, wherein at least one implantable lead of the input and output links is longer than approximately 2 inches.

6. The hearing assistance system of claim 4, wherein at least one implantable lead of the input and output links comprises first and second lead wires.

7. The hearing assistance system of claim 4, wherein at least one implantable lead of the input and output links comprises first and second lead wires that are twisted with each other.

8. The hearing assistance system of claim 4, wherein at least one implantable lead of the input and output links comprises at least one shielded lead wire.

9. The hearing assistance system of claim 1, and further comprising:

an input link electrically connecting the input transducer to the electronics unit and an output link electrically connecting the electronics unit to the output stimulator, wherein at least one of the input and output links is capable of alternating current coupled communication.

10. The hearing assistance system of claim 1, wherein the electronics unit includes a power source.

11. The hearing assistance system of claim 10, wherein the power source includes a battery having capacity exceeding 1 ampere-hour.

12. The hearing assistance system of claim 1, wherein the electronics unit includes a digital signal processor.

13. The hearing assistance system of claim 1, wherein the electronics unit includes a telemetry device for communicating with an external telemetry unit.

14. The hearing assistance system of claim 1, wherein the middle ear region in which the input transducer and output stimulator are proportioned for disposition is a naturally present cavity.

15. A hearing assistance system comprising:

an electromechanical input transducer, proportioned for disposition within a middle ear region of a first ear, for converting a mechanical sound vibration into an input electrical signal;

an output stimulator, proportioned for disposition within the middle ear region of the first ear;

an electronics unit having a volume exceeding approximately 10 cubic centimeters, proportioned only for subcutaneous pectoral implantation remotely from the input transducer and the output stimulator, that provides an output electrical signal in response to the input electrical signal;

an input link electrically connecting the input transducer to the electronics unit for communicating the input electrical signal between the input transducer and the electronics unit; and an output link electrically connecting the output stimulator to the electronics unit for communicating the output electrical signal between the output stimulator and the electronics unit.

16. The system of claim 1 wherein the electromechanical input transducer is configured and arranged for connection to a tympanic membrane, a malleus, or an incus of the middle ear region of the first ear.

17. The system of cliam 1 wherein the output stimulator is configured and arranged for connection to a stapes of the middle ear region of the first ear or a cochlea of the inner ear region of the first ear.

18. A hearing assistance system comprising:

an electromechanical input transducer, proportioned for disposition within a middle ear region of a first ear, for converting a mechanical sound vibration into an input electrical signal;

an output stimulator, proportioned for disposition within at least one of the middle ear region and an inner ear region of a second ear; and an electronics unit having a volume exceeding approximately 10 cubic centimeters, electrically connected between the input transducer and the output stimulator and proportioned only for subcutaneous pectoral implantation, wherein the electronics unit receives the input electrical signal from the input transducer in the first ear and provides an output electrical signal to the output stimulator in the second ear in response to the input electrical signal.

* * * * *